United States Patent
Schwarz et al.

(10) Patent No.: US 10,914,675 B2
(45) Date of Patent: Feb. 9, 2021

(54) SENSOR DEVICE FOR MEASURING A FLUID CONCENTRATION, AND USE OF THE SENSOR DEVICE

(71) Applicant: Robert Bosch GmbH, Stuttgart (DE)

(72) Inventors: Mike Schwarz, Kusterdingen (DE); Thomas Friedrich, Reutlingen (DE); Timon Brueckner, Reutlingen (DE)

(73) Assignee: Robert Bosch GmbH, Stuttgart (DE)

( * ) Notice: Subject to any disclaimer, the term of this patent is extended or adjusted under 35 U.S.C. 154(b) by 149 days.

(21) Appl. No.: 15/740,477

(22) PCT Filed: May 25, 2016

(86) PCT No.: PCT/EP2016/061734
§ 371 (c)(1),
(2) Date: Dec. 28, 2017

(87) PCT Pub. No.: WO2017/005404
PCT Pub. Date: Jan. 12, 2017

(65) Prior Publication Data
US 2018/0188157 A1  Jul. 5, 2018

(30) Foreign Application Priority Data

Jul. 9, 2015 (DE) .................. 10 2015 212 870

(51) Int. Cl.
*G01N 21/25* (2006.01)
*G01N 21/3504* (2014.01)
(Continued)

(52) U.S. Cl.
CPC .............. *G01N 21/255* (2013.01); *G01J 3/36* (2013.01); *G01J 3/42* (2013.01); *G01N 21/27* (2013.01);
(Continued)

(58) Field of Classification Search
CPC .................................................. G01N 33/0031
(Continued)

(56) References Cited

U.S. PATENT DOCUMENTS 5,285,131 A * 2/1994 Muller .................... G01J 3/108
313/315
5,341,214 A    8/1994 Wong
(Continued)

FOREIGN PATENT DOCUMENTS

CN          1216108 A     5/1999
CN        102762975 A    10/2012
(Continued)

OTHER PUBLICATIONS

International Search Report dated Sep. 2, 2016, of the corresponding International Application PCT/EP2016/061734 filed May 25, 2016.

*Primary Examiner* — David P Porta
*Assistant Examiner* — Carolyn Fin
(74) *Attorney, Agent, or Firm* — Norton Rose Fulbright US LLP; Gerard Messina

(57) ABSTRACT

A sensor apparatus having a sensor unit. The sensor unit including pixel assemblages on a substrate upper side of a substrate located on a lower side of the sensor unit; a cap, on the substrate upper side, which covers the pixel assemblages, a cavity being formed between the substrate upper side and the cap; a plurality of filters that are transparent to wavelength regions that differ from one another, exactly one pixel assemblage being associated with each filter; and the filters being on the cap so that the infrared radiation propagated through an absorption gap of the sensor apparatus and the upper side of the sensor unit is detectable, through the respective filter, by the pixel assemblage associated with the respective filter; and a coating made of a light-absorbing and/or light-reflecting material being configured at least
(Continued)

locally on a part of the cap which is not covered by the filters.

7 Claims, 3 Drawing Sheets

(51) Int. Cl.
*G01N 21/31* (2006.01)
*G01J 3/36* (2006.01)
*G01J 3/42* (2006.01)
*G01N 21/27* (2006.01)
*G01N 33/00* (2006.01)
*G01J 3/12* (2006.01)

(52) U.S. Cl.
CPC ....... *G01N 21/314* (2013.01); *G01N 21/3504* (2013.01); *G01N 33/004* (2013.01); *G01J 2003/1213* (2013.01); *G01N 2021/3137* (2013.01); *G01N 2021/3166* (2013.01)

(58) Field of Classification Search
USPC .......................... 250/339.06, 339.02, 339.01
See application file for complete search history.

(56) References Cited

U.S. PATENT DOCUMENTS

| | | | | |
|---|---|---|---|---|
| 5,650,624 | A | 7/1997 | Wong | |
| 5,962,854 | A * | 10/1999 | Endo | G01J 5/02 |
| | | | | 250/338.1 |
| 2012/0171423 | A1 * | 7/2012 | Haines | B32B 5/16 |
| | | | | 428/148 |

FOREIGN PATENT DOCUMENTS

| | | |
|---|---|---|
| DE | 10360215 A1 | 7/2005 |
| DE | 102006004003 A1 | 10/2006 |
| JP | H06229829 A | 8/1994 |
| WO | 2005/045404 A1 | 5/2005 |

* cited by examiner

SENSOR DEVICE FOR MEASURING A FLUID CONCENTRATION, AND USE OF THE SENSOR DEVICE

FIELD

The present invention relates to a sensor apparatus, and to a use of a sensor apparatus, for measuring a fluid concentration. The invention relates in particular to a sensor apparatus for detecting carbon dioxide gas and for measuring the concentration of carbon dioxide gas.

BACKGROUND INFORMATION

Sensors for measuring fluid concentrations, in particular the concentration of carbon dioxide gas, have a wide variety of utilization capabilities, for example for monitoring air quality or in safety engineering. PCT Application No. WO 2005/045404 A1 describes an infrared gas sensor that can measure a gas concentration by the fact that infrared radiation that is propagated through an absorption gap filled with the gas to be measured is detected through a first filter by a first sensing unit, and is detected through a second filter by a second sensing unit, a concentration of the gas being measured on the basis of a difference in the intensities of the detected radiation.

Cross-sensitivity of the sensing units can occur in a gas sensor of this kind because radiation that passes through between the filters can also be sensed by the sensing units.

SUMMARY

The present invention relates to a sensor apparatus, and a use of a sensor apparatus.

According to a first aspect, the present invention provides a sensor apparatus having an absorption gap, located in an at least partly closed sample space, for reception of a fluid to be analyzed. Located at one end of the absorption gap is a radiation source for emitting infrared radiation into the absorption gap, the infrared radiation emitted into the absorption gap being directed onto an upper side of a sensor unit located at the other end of the absorption gap. The sensor unit has a plurality of pixel assemblages each having at least one pixel, which are disposed on a substrate upper side of a substrate located on a lower side of the sensor unit. A cap that covers the pixel assemblages is disposed on the substrate upper side, a cavity being formed between the substrate upper side and the cap. The sensor further has a plurality of filters that are transparent to wavelength regions that differ at least in part from one another, exactly one pixel assemblage being associated with each filter; and the filters being disposed on the cap in such a way that the infrared radiation propagated through the absorption gap and through the upper side of the sensor unit is detectable, through the respective filter, by the pixel assemblage associated with the respective filter. A coating made of a light-absorbing and/or light-reflecting material is configured at least locally on a part of the cap which is not covered by the filters.

According to a further aspect, the present invention provides a use of a sensor apparatus for measuring a fluid concentration, a concentration of the fluid being calculated based on a comparison of the intensities of the infrared radiation detected by the respective pixel assemblages.

Preferred refinements of the present invention are described herein.

In accordance with the present invention, the cap that covers the pixel assemblages is substantially transparent to infrared radiation so as to guarantee that the radiation reaches the pixel assemblages. The coating, however, prevents infrared radiation from passing through that part of the cap which is located between the filters, and being detected by the pixel assemblages. This ensures that a specific pixel assemblage detects only the infrared radiation that is irradiated through the filter associated with the pixel assemblage. The accuracy of the sensor apparatus is thus enhanced, and a concentration of the fluid can be measured with greater precision. Cross-sensitivity, due to scattered light that enters through that part of the cap which is not covered by filters, is prevented.

According to a further embodiment of the sensor apparatus, at least one pixel assemblage of the plurality of pixel assemblages is embodied as a reference pixel assemblage, and the filter associated with the reference pixel assemblage is transparent in a wavelength region that is less strongly absorbed by a specified fluid, in particular carbon dioxide gas, than the wavelength regions to which the remaining filters are transparent. The intensity of the infrared radiation acquired by the reference pixel assemblage is very largely independent of the concentration of the fluid to be detected, since the radiation that is allowed to pass through the filter associated with the reference pixel assemblage is absorbed very little or not at all by the fluid. In contrast thereto, the intensity of the radiation that is detected by the remaining reference pixel assemblages depends more strongly on a concentration of the fluid. At a high fluid concentration, more radiation is absorbed in the wavelength region in which the filters associated with the remaining pixel assemblages are transparent. The difference between the infrared radiation sensed by the reference pixel assemblage and the infrared radiation sensed by the remaining pixel assemblages therefore depends on the concentration of the fluid. By first calibrating the sensor apparatus with a control gas having a known concentration of the fluid to be checked, it is thus possible to use the sensor apparatus to determine a fluid concentration.

According to a further embodiment of the sensor apparatus, the coating is made of a metal, of a nitride compound, and/or of an oxide compound. These coatings exhibit good light-absorbing and/or light-reflecting properties.

According to a further embodiment of the sensor apparatus, the coating is made of heavily doped silicon. Heavily doped silicon is likewise largely opaque to infrared radiation.

According to a further embodiment of the sensor apparatus, the coating has a surface texture. The reflecting or absorbing property of the material is increased by suitable selection of this surface texture, and the transparency of the coating to infrared radiation is thus additionally decreased.

According to a further embodiment of the sensor apparatus, the radiation source encompasses a laser diode, a hot wire, an incandescent lamp, or a light-emitting diode.

According to a further embodiment of the sensor apparatus, the absorption gap has a reflector for deflecting the infrared radiation. As a result thereof, in particular, the radiation source and the sensor unit can be mounted on the same substrate. The infrared light emitted from the radiation source substantially perpendicularly to the substrate is then deflected with the aid of the reflector in such a way that it strikes the sensor unit. The absorption gap can furthermore thereby be lengthened.

According to a further embodiment of the sensor apparatus, the coating covers the entire part of the cap not covered by the filter. As a result, light can propagate only through the filters, thereby completely preventing cross-sensitivity due to light that passes through the cap but not through the filters.

BRIEF DESCRIPTION OF THE DRAWINGS

Unless otherwise indicated, identical or functionally identical elements and apparatuses are labeled with the same reference characters in all the Figures.

DETAILED DESCRIPTION OF EXAMPLE EMBODIMENTS

Figure 1:
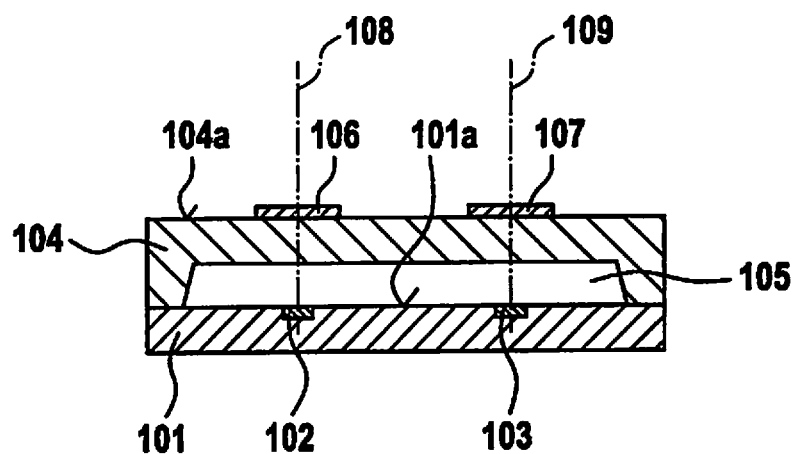
FIG. 1 is a schematic cross-sectional view to explain a sensor apparatus in accordance with the present invention.

FIG. 1 is a schematic cross-sectional view to explain a sensor apparatus in accordance with the present invention. A first pixel assemblage 102 and a second pixel assemblage 103 are located on a first substrate upper side 101a of a first substrate 101 that is constituted, for example, by a silicon wafer. Pixel assemblages 102, 103 can have a plurality of pixels that are embodied to detect infrared radiation. An intensity of an infrared radiation sensed by first pixel assemblage 102 and by second pixel assemblage 103 can be calculated via a measurement device (not shown) connected to pixel assemblages 102, 103. Optionally, only a difference in the intensities of the infrared radiation detected by first pixel assemblage 102 and detected by second pixel assemblage 103 can also be measured. First pixel assemblage 102 and second pixel assemblage 103 are preferably of identical construction, i.e. they have an identical measurement sensitivity.

A cap 104 made of a material transparent to infrared light, preferably silicon, is disposed on first substrate surface 101a. Cap 104 covers first pixel assemblage 102 and second pixel assemblage 103 in such a way that a cavity 105 is formed between first substrate surface 101a and cap 104.

A first filter 106 and a second filter 107 are disposed on a cap upper side 104a, facing away from substrate 101, of cap 104. First filter 106 is associated with first pixel assemblage 102 and is located substantially directly above first pixel assemblage 102, while second filter 107 is associated with second pixel assemblage 103 and is located substantially directly above second pixel assemblage 103. In other words, first filter 106 and second filter 107 respectively intersect a first axis 108 and a second axis 109 that proceed, perpendicularly to first substrate 101, through the center point respectively of first pixel assemblage 102 and of second pixel assemblage 103.

First filter 106 and second filter 107 are monochromators. Second filter 107 is transparent to a wavelength that is absorbed by the fluid, while first filter 106 is transparent to a wavelength that is absorbed very little or not at all by the fluid. If the sensor apparatus is used to detect carbon dioxide, second filter 107 is then transparent to a wavelength that is particularly strongly absorbed by carbon dioxide, for example a wavelength between 4.1 µm and 4.35 µm, preferably 4.26 µm. First filter 106, conversely, is transparent to a reference wavelength that is absorbed very little or not at all by carbon dioxide, for example a wavelength between 3.5 µm and 4 µm, preferably 3.9 µm.

Figure 2:
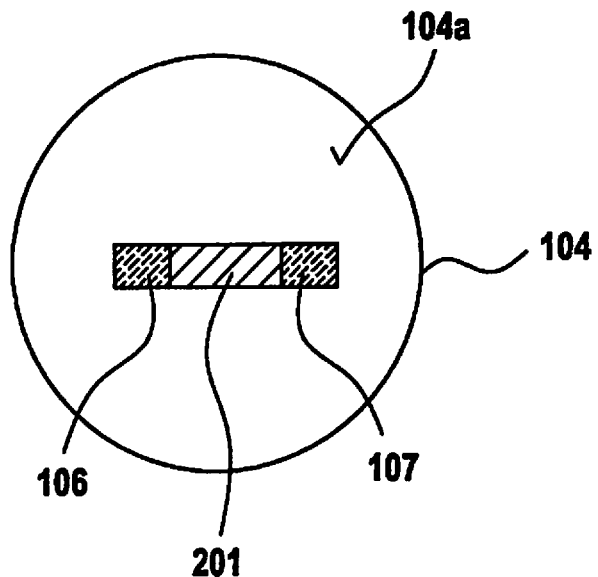
FIG. 2 is a sectional view of part of a sensor apparatus in accordance with a first embodiment of the present invention.

FIG. 2 is a plan view of a cap 104 in accordance with a first embodiment of the present invention. That region of a cap upper side 104a of cap 104 which is located between first filter 106 and second filter 107 is coated with a coating 201. Coating 201 is made of a material that absorbs or reflects infrared light. The coating can be made, for example, of a metal, a nitride compound, an oxide compound, and/or heavily doped silicon. The coating can also have been applied, for example, by chemical gas-phase deposition.

Coating 201 is preferably made up of a reflective layer, since this, in contrast to an absorbent layer, heats up less intensely. This prevents coating 201 from radiating into cavity 105.

Figure 3:
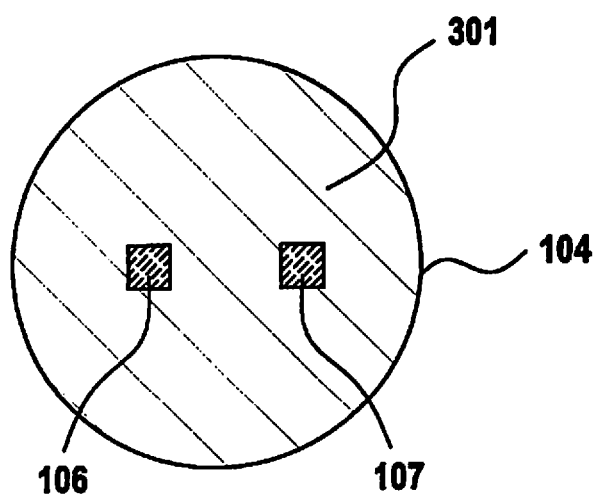
FIG. 3 is a sectional view of part of a sensor apparatus in accordance with a second embodiment of the present invention.

As shown in FIG. 3, a coating 301 can also coat the entire cap upper side 104a that is not covered by first filter 106 and by second filter 107. The result is that cap upper side 104a is transparent to infrared radiation only in those regions in which first filter 106 and second filter 107 are located.

In addition, the absorbing and/or reflecting property of coating 201 in accordance with the first embodiment, or of coating 301 in accordance with the second embodiment, can be increased by way of a surface texture. For example, coating 201, 301 can be roughened, for example using an etching method.

Figure 4:
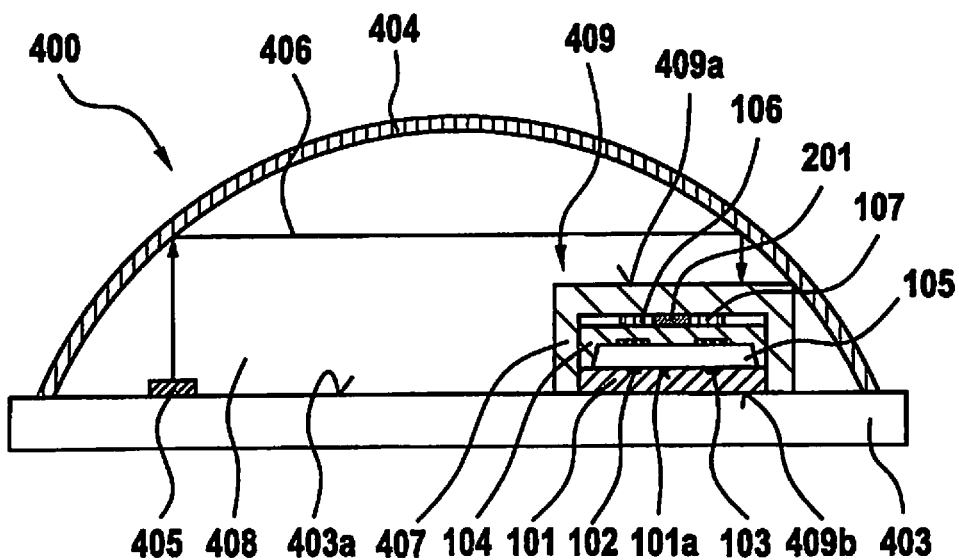
FIG. 4 is a schematic cross-sectional view of a sensor apparatus in accordance with the first embodiment of the present invention.

A sensor apparatus in accordance with a first embodiment of the present invention is illustrated in FIG. 4. The above-described first substrate 101 is disposed on a portion of a second substrate upper side 403a of a second substrate 403 that is constituted, for example, by a silicon wafer, first substrate upper side 101a facing away from second substrate upper side 403a. First substrate 101 encompasses first pixel assemblage 102 and second pixel assemblage 103, which are covered by cap 104. First filter 106 and second filter 107 are disposed on cap 104, a coating 201 being constituted, as shown in FIG. 2, between first filter 106 and second filter 107.

Also disposed on second substrate 403 is a molding compound that forms a cover 407 and covers and protects first substrate 101 and the coated cap 104 having first filter 106 and second filter 107. Cover 407 is made of a material that is transparent to infrared light.

First substrate 101 having first pixel assemblage 102 and second pixel assemblage 103, the coated cap 104, and cover 407 form a sensor unit 409, first substrate 101 being located on a sensor unit lower side 409b of the sensor unit, and cover 407 being located on a sensor unit upper side 409a of the sensor unit.

Disposed on second substrate 403 at a distance from sensor unit 409 is a radiation source 405 that is embodied to emit infrared light. Radiation source 405 can be, for example, a laser diode, a hot wire, an incandescent lamp, or a light-emitting diode. Radiation source 405 can be made up in particular of infrared diodes that are embodied as arrays. Radiation 406 emitted from radiation source 405 can be narrow-band, for example in the wavelength region from 2 to 14 µm. The invention is not, however, limited thereto. The radiation source can thus also emit broad-band light, for example thanks to the use of a hot wire.

Radiation source 405 and sensor unit 409 are covered in domed fashion by a reflector 404 made, for example, of metal, which is likewise disposed on second substrate 403. In sample space 400 thereby defined, an absorption gap 408 is located between radiation source 405 and sensor unit 409. Radiation source 405 emits radiation 406; for illustration, only one light beam is shown. When laser diodes are used, radiation 406 can be emitted substantially perpendicularly to second substrate 403. The invention is not, however, limited thereto. When a hot wire is used, for example, radiation 406 can be emitted in all directions from the substrate.

Sample 400 is configured with apparatuses (not shown) for admitting and releasing the fluid to be analyzed, for example carbon dioxide gas.

Radiation 406 emitted from radiation source 405 propagates through absorption gap 408; it is reflected, possibly several times, at reflector 404 and ultimately strikes sensor unit upper side 409a of sensor unit 409. Radiation 406 thereby interacts in absorption gap 408 with the fluid present in absorption gap 408, specific wavelength regions of radiation 406 being absorbed by the fluid.

Radiation 406 passes through the transparent cover 407 and strikes cap upper side 104a of cap 104. Radiation 406 cannot propagate through that part of cap 104 which is covered by coating 201, but instead is reflected or absorbed by coating 201. First pixel assemblage 102 detects the light propagated through first filter 106, and second pixel assemblage 103 detects the light propagated through second filter 107.

Because filter 106 is transparent to a wavelength region that is absorbed very little or not at all by the fluid, for example carbon dioxide, the intensity of the radiation sensed by first pixel assemblage 102 is substantially independent of the fluid concentration in absorption gap 408. First pixel assemblage 102 therefore serves as a reference pixel assemblage.

In contrast thereto, second filter 107 is transparent to a wavelength region that is absorbed by the fluid, so that the intensity of the radiation sensed by second pixel assemblage 103 is dependent on the fluid concentration present in absorption gap 408. First pixel assemblage 102 and second pixel assemblage 103 can be evaluatable separately, i.e. individually; or only the intensity difference between the radiation sensed by first pixel assemblage 102 and the radiation sensed by second pixel assemblage 103 can be detected. That difference is evaluated by an evaluation apparatus (not shown).

The correlation between the difference and the fluid concentration can be determined by calibrating the sensor apparatus with the aid of a fluid of known fluid concentration, for example a reference carbon dioxide gas. At a higher fluid concentration, for example, the measured intensity difference is likewise higher. As a result, the sensor apparatus can be used to measure a fluid concentration.

Figure 5:
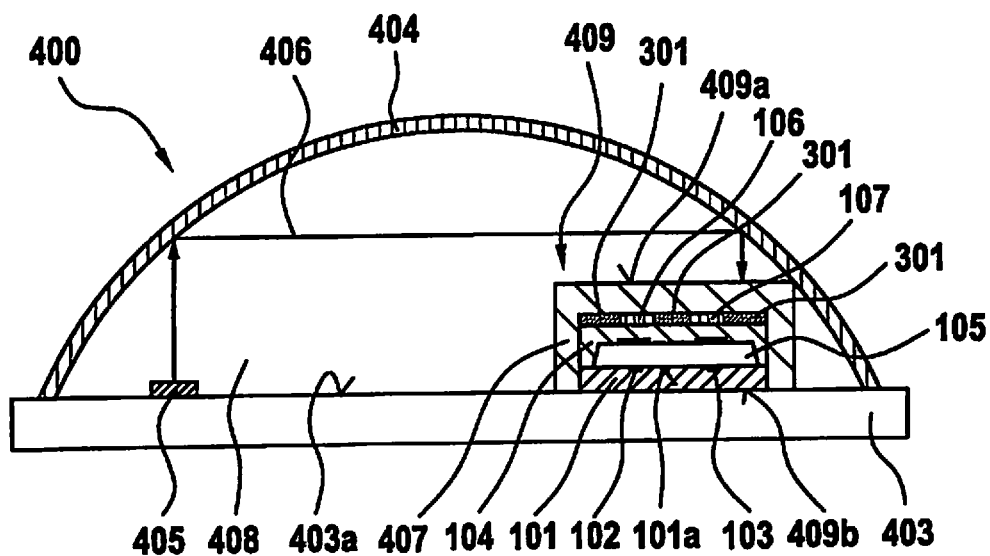
FIG. 5 is a schematic cross-sectional view of a sensor apparatus in accordance with the second embodiment of the present invention.

FIG. 5 shows a sensor apparatus in accordance with the second embodiment of the present invention. In contrast to the first embodiment, here the entire cap upper side 104a of cap 104, as shown in FIG. 3, is equipped with a coating 301. This ensures that no radiation 406 can pass through a part of cap 104 not covered by first filter 106 and by second filter 107, and be sensed by first pixel assemblage 102 and second pixel assemblage 103. This ensures that first pixel assemblage 102 detects only radiation 406 that is propagated through first filter 106, and second pixel assemblage 103 detects only radiation 406 that is propagated through second filter 107. The accuracy with which the fluid concentration is measured is thereby increased.

What is claimed is:

1. A sensor apparatus, comprising:
    an absorption gap located in an at least partly closed sample space, wherein the absorption gap is configured for reception of a fluid to be analyzed;
    a radiation source located at a first end of the absorption gap, wherein the radiation source is configured for emitting infrared radiation into the absorption gap, the infrared radiation emitted into the absorption gap directable onto an upper side of a sensor unit located at a second end of the absorption gap; and
    the sensor unit, the sensor unit including:
        a plurality of pixel units, each pixel unit having at least one pixel, wherein the plurality of pixel units are disposed on an upper side of a substrate, the substrate is located on a lower side of the sensor unit,
        a cap, disposed on the upper side of the substrate, wherein the cap covers the plurality of pixel units,
        a cavity being formed between the upper side of the substrate and the cap, and
        a plurality of filters that are transparent to wavelength regions that differ at least in part from one another, each of the plurality of filters being associated with exactly one of the plurality of pixel units, the filters being disposed on the cap in such a way that the infrared radiation directed onto the upper side of the sensor unit is propagated through the upper side of the sensor unit and is detectable, through each of the plurality of filters, by the exactly one of the plurality of the pixel units associated with each of the plurality of filters,
    wherein the cap is made of a material transparent to infrared light, and
    wherein a coating is made of at least one of a light-absorbing material and a light-reflecting material, wherein the coating is disposed on a part of the cap which is not covered by the filters, wherein the coating is located only between the plurality of filters.

2. The sensor apparatus as recited in claim 1, wherein at least one pixel unit of the plurality of pixel units is embodied as a reference pixel unit, and the filter associated with the reference pixel unit is transparent in a wavelength region that is less strongly absorbed by carbon dioxide gas, than the wavelength regions to which the remaining filters are transparent.

3. The sensor apparatus as recited in claim 1, wherein the coating is made of at least one of: (i) a metal, (ii) a nitride compound, and (iii) an oxide compound.

4. The sensor apparatus as recited in claim 1, wherein the coating is made of heavily doped silicon.

5. The sensor apparatus as recited in claim 1, wherein the coating has a surface texture.

6. The sensor apparatus as recited in claim 1, wherein the radiation source encompasses one of a laser diode, a hot wire, an incandescent lamp, or a light-emitting diode.

7. The sensor apparatus as recited in claim 1, wherein the absorption gap has a reflector for deflecting the infrared radiation.

* * * * *